United States Patent [19]

Russek

[11] Patent Number: 5,319,355
[45] Date of Patent: Jun. 7, 1994

[54] ALARM FOR PATIENT MONITOR AND LIFE SUPPORT EQUIPMENT SYSTEM

[76] Inventor: Linda G. Russek, The Russek Foundation 1200 N. Federal Highway, Suite 209, Boca Raton, Fla. 33432

[21] Appl. No.: 727,308

[22] Filed: Jul. 10, 1991

Related U.S. Application Data

[63] Continuation-in-part of Ser. No. 666,266, Mar. 6, 1991, abandoned.

[51] Int. Cl.$^5$ .................... G08B 23/00; A61M 16/00; H04Q 1/30
[52] U.S. Cl. .................... 340/573; 128/202.22; 128/903; 340/311.1; 340/407.1; 340/502; 340/525; 455/53.1; 455/351
[58] Field of Search ................ 340/573, 311.1, 825.44, 340/524-525, 407, 539, 514, 502; 128/903, 202.22; 455/351, 53-54, 100, 88-90, 53.1, 54.1, 54.2; 368/10-12

[56] References Cited

U.S. PATENT DOCUMENTS

| | | | |
|---|---|---|---|
| D. 285,964 | 9/1986 | Ziebol | D24/17 |
| 3,852,736 | 12/1974 | Cook et al. | 340/515 |
| 3,877,467 | 4/1978 | Pilechi | 128/202.22 |
| 4,025,918 | 5/1977 | Beauchamp | 340/502 |
| 4,155,357 | 5/1979 | Dahl | 128/202.22 |
| 4,316,182 | 2/1982 | Hodgson | 340/606 |
| 4,550,726 | 11/1988 | McEwen | 128/202.22 |
| 4,558,300 | 12/1985 | Goldman | 340/286.14 |
| 4,692,742 | 9/1987 | Raizen et al. | 340/539 |

(List continued on next page.)

OTHER PUBLICATIONS

Motorola, "STX" Portable Radio, 1987.
Motorola, Nurse Call Paging Systems, 1988.
Motorola, "Midas" Digital Alerting System, 1989.
Motorola, "Wrist Watch Pager", 1990.
McIntyre et al., "Application of Automated Human Voice Delivery to Warning Devices in an Intensive Care Unit: A Laboratory Study", Jul. 1989.
Navabi et al., "Integrated Monitoring Can Detect Critical Events and Improve Alarm Accuracy", Jul.-Aug. 1991.
Pacela, "From the Publisher's Desk-Synergistic Monitoring", Journal of Clinical Engineering, 1991.
Gottschalk, "The Medical Information Bus-Overview of the Medical Device Data Language", Journal of Clinical Engineering, Jul.-Aug. 1991.
Shabot et al., "Decision Support Alerts for Clinical Laboratory and Blood Gas Data", 1990.
"Alarm Display Unit", Marquette Electronics, date unknown.
"Personal Cardiograph", Marquette Electronics, date unknown.

(List continued on next page.)

Primary Examiner—Thomas Mullen
Attorney, Agent, or Firm—Hamilton, Brook, Smith & Reynolds

[57] ABSTRACT

An alarm system for notifying necessary medical and hospital personnel that a patient or the patient's life support equipment require immediate response without providing the alarm signal to the monitored patient or surrounding patients, to prevent patient trauma which may otherwise result from the sound of the alarm. The system includes an alarm signal generator that provides a coded pulse indication of the patient and equipment type. The coded signal is sent to a master control unit preferably located at a nurses' station. The master control unit then transmits the coded alarm signal simultaneously to the appropriate group of pagers having vibrational annunciators and a visual display that describes the patient location and equipment type. The patients monitor and equipment at bedside and the pagers have no audio alarm signals. The alarm signal can only be terminated manually by an interrupt switch at the bedside.

21 Claims, 5 Drawing Sheets

U.S. PATENT DOCUMENTS

| | | | |
|---|---|---|---|
| 4,786,889 | 11/1988 | Hayasaka | 340/311.1 |
| 4,794,392 | 12/1988 | Selinko | 340/825.46 |
| 4,802,550 | 2/1989 | Poore | 181/131 |
| 4,803,471 | 2/1989 | Rowland | 340/626 |
| 4,827,943 | 5/1989 | Bornn et al. | 128/903 X |
| 4,864,283 | 9/1989 | Seto | 340/502 X |
| 4,879,759 | 11/1989 | Matsumoto et al. | 455/348 |
| 4,918,438 | 4/1990 | Yamasaki | 340/825.46 |
| 5,003,984 | 4/1991 | Muraki et al. | 128/903 X |

OTHER PUBLICATIONS

"MAC-6: Computerized Electrocardiograph", Marquette Electronics, date unknown.

"MAC-15: Five Electrocardiographic Instruments In One", Marquette Electronics, date unknown.

"MAX-1: Exercise and Resting Electrocardiography", Marquette Electronics, date unknown.

Advertisement for TRAM Modules, Marquette Electronics, date unknown.

"Unity-The Power of Integrated Patietn Monitoring", Marquette Electronics, date unknown.

"BRAVO Alphanumeric Pager", Motorola, date unknown.

"Binary Paging Capability for MSR 2000 Stations", Motorola, date unknown.

"Mid-Band MX1000 Series Select 5 (68-88 MHz) Portable Radio", Motorola, date unknown.

"MT1000 Series 'Handie Talkie' Synthesized FM Portable Radio", Motorola, date unknown.

"PMR 2000 Personal Message Receiver", Motorola, date unknown.

"PORTA PAK On-Site Communications System", Motorola, date unknown.

"Wrist Watch Pager", Motorola, date unknown.

"SPECTRA Mobile Radio", Motorola, date unknown.

PAGENET brochure for Motorola Pager, date unknown.

"STX Series Handie-Talkie Portable Radio", Motorola, date unknown.

"Remote Alarm Paging System", Motorola, date unknown.

"BRAVO Tone and Visual/Silent and Visual Alert Pager", Motorola, date unknown.

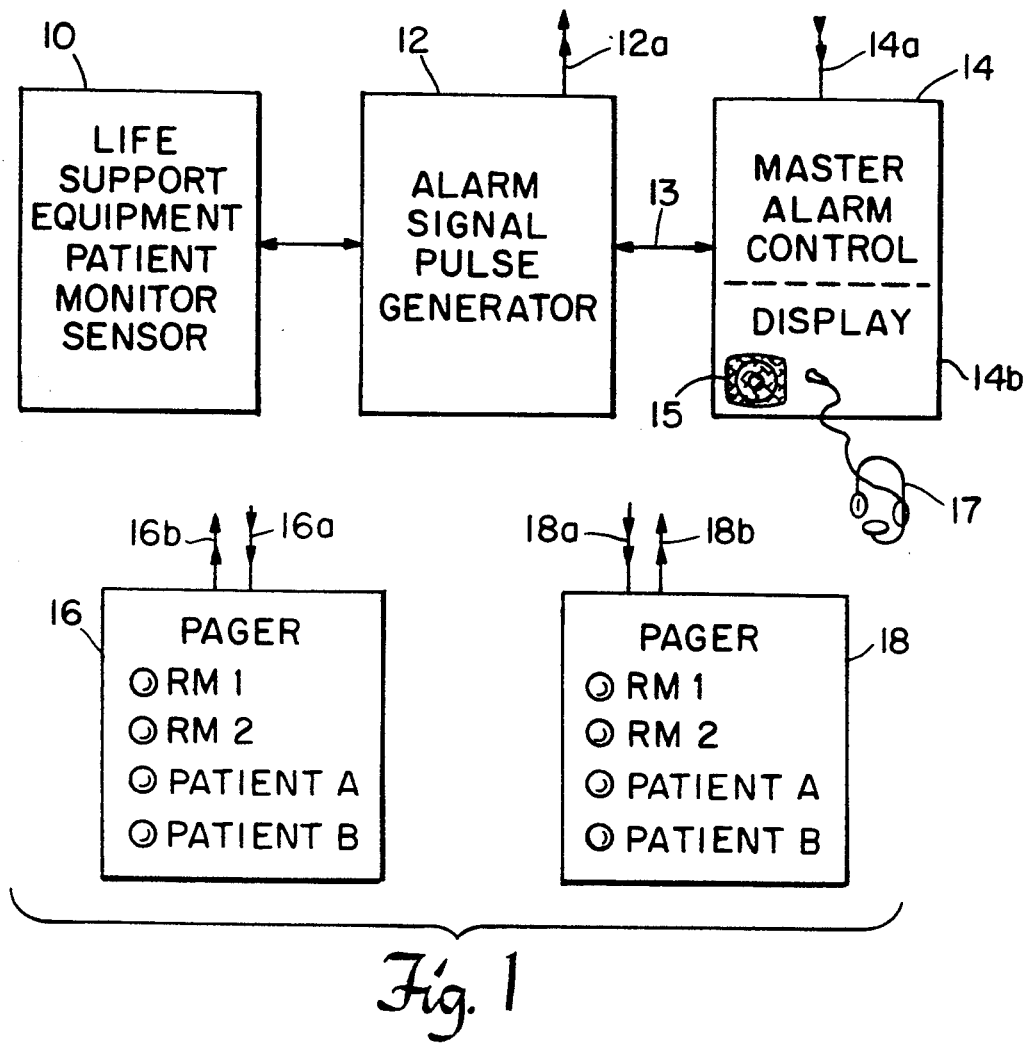
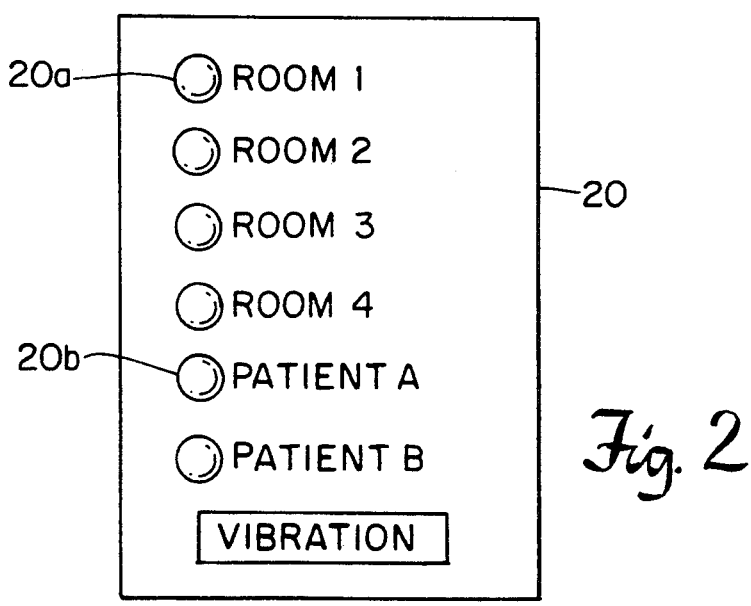
Fig. 1
Fig. 2

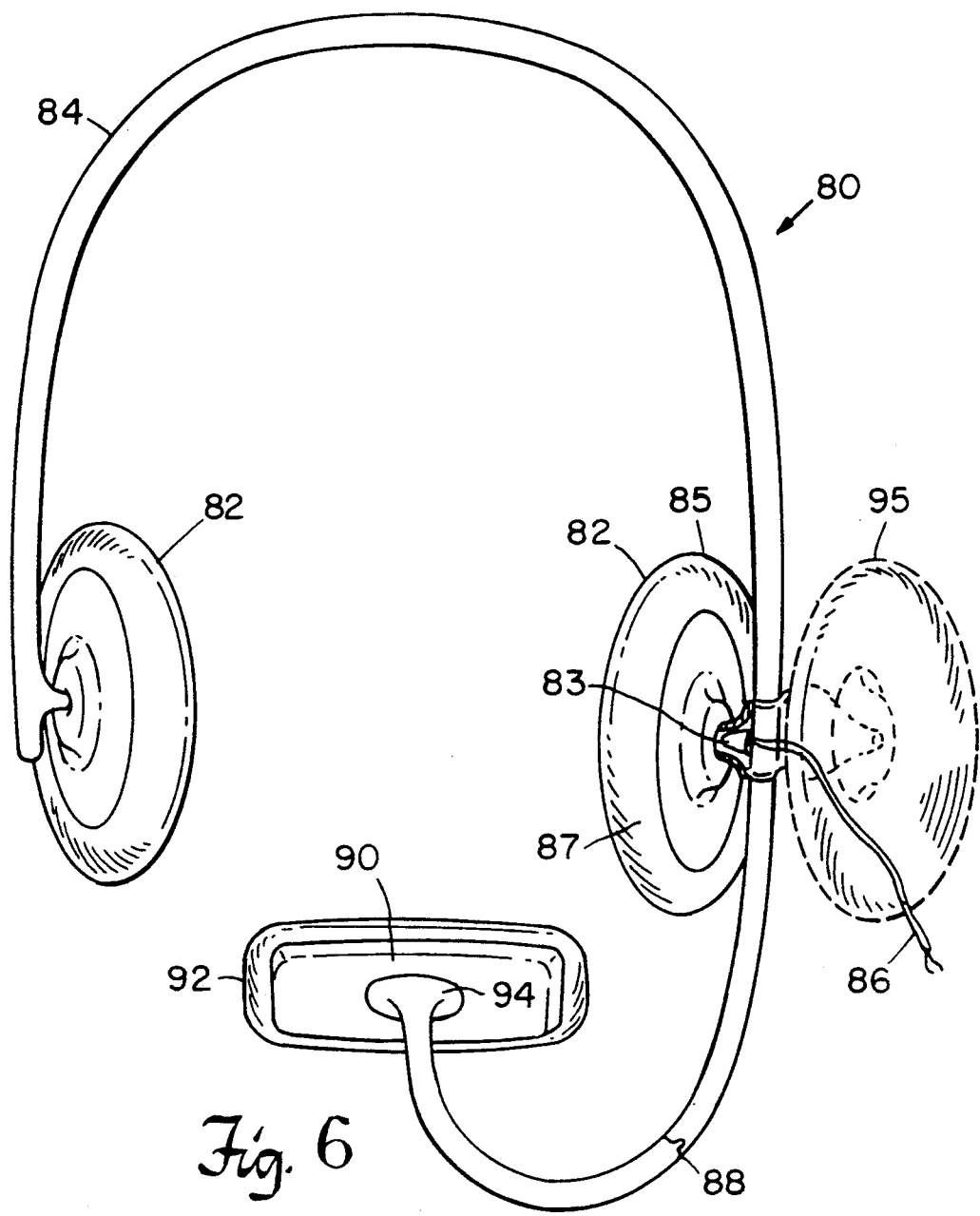
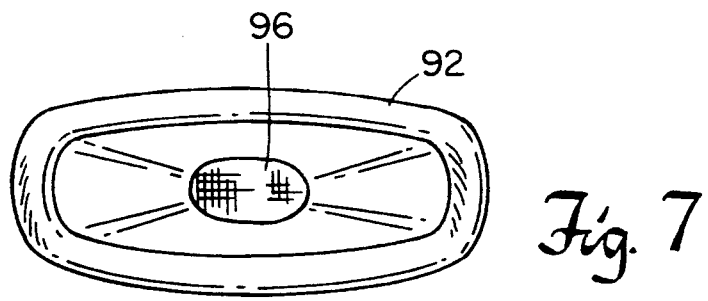
Fig. 6
Fig. 7

ALARM FOR PATIENT MONITOR AND LIFE SUPPORT EQUIPMENT SYSTEM

This application is a continuation-in-part of application Ser. No. 07/666,266, filed Mar. 6, 1991, abandoned.

BACKGROUND OF THE INVENTION

1. Field of the Invention

This invention relates generally to a communications and alarm system for providing secure and reliable patient monitoring and also for monitoring the operational status of various types of medical equipment such as, but not limited to, intravenous feeding devices, defibrillators, ventilators, EKG, EEG and pulse monitors. The equipment used with the present system includes emergency equipment employed in a pre-hospital setting, such as in ambulances or at the site of accidents; equipment in post-hospital settings, such as in a patient's home, in a nursing home, in a hospice, in a Doctor's office, in a clinic or at medical teaching institutions and equipment used in the hospital such as in the recovery room or in the operating room.

The invention is capable of providing a means for communicating medical information over long distances and for immediately summoning the appropriate medical and hospital personnel to the patient in need of help. The invention is silent and unobservable to the patient to prevent unnecessary stress or trauma. The system can also reduce the stress level of the medical and hospital staff and other patients. Another aspect of the present invention is to provide monitoring equipment that can be conveniently worn on medical personnel in order to foster communications that indicate more information to the user and for hospital administrators. A further aspect of the invention is to provide for a communications system that enables medical personnel to remotely test the operational status of medical equipment and provide better staffing management for medical emergencies communicated by the system.

2. Description of the Prior Art

Critically ill patient and life support equipment monitors and alarm systems are well known. Typically, the monitor includes an audio alarm located next to the patient's bed attached to the patient's life support medical equipment. Intravenous (IV) feeders and ventilators are examples of life support equipment that include an audio alarm if the equipment should malfunction or stop completely. The principal problem with these alarm devices is the stress and trauma that the audio alarm can render to a critically ill patient. Not only is the audio alarm sound often startling to the patient, but it could also trigger a panic state with corresponding psycho-physiology contributing to or resulting in the inability to marshal an adequate defense against disease.

Examples of intensive alarm systems abound. For example, U.S. Pat. No. 4,803,471 shows a ventilator monitor and alarm apparatus issued to Rowland on Feb. 7, 1989. U.S. Pat. No. 4,550,726 issued to McEwen on Nov. 5, 1985 shows a method and apparatus for the detection of breathing gas interruption typically for a ventilator; U.S. Pat. No. 4,155,375 issued to Dahl, May 22, 1979, discloses a patient ventilator disconnect alarm which causes an audible alarm condition; U.S. Pat. No. 3,877,467 shows an artificial U.S. Pat. No. 4,316,182 issued to Hodgson Feb. 16, 1982 shows a ventilator disconnection alarm. All of these alarm systems basically provide for audio and/or visual alarms at the patient's bedside. Because the sound alert is placed within the hearing range of the patient, however, the alarm sound can greatly disturb, if not traumatize, the patient and, in fact, exacerbate the patient's decline toward death.

Small pocket sized paging devices which provide audio and tactile vibrational signals to alert the person carrying a pager of a remote call or message also are known. U.S. Pat. No. 4,879,759 issued to Matsumoto, et al. Nov. 7, 1989, for example, shows a pager with the extra function of a vibrator. Also, U.S. Pat. No. 4,918,438 shows a paging receiver having an audible and a vibrator annunciating means issued to Yamasaki, Apr. 17, 1990. U.S. Pat. No. 4,786,889 issued to Hayasaka shows a battery casing for a paging receiver which includes a vibrating housing for alerting someone through a pager without audible sound. U.S. Pat. No. 4,794,392 issued to Selinko on Dec. 27, 1988, describes a vibrator alert device for a communication receiver, which is essentially a paging device.

Although the prior art paging equipment does show the use of vibration with or without an audio sound, heretofore such paging equipment does not function in combination with a communications system linked to medical equipment to provide a non-audible and more critically, automatic alarm to doctors, technicians and nurses in the patient vicinity without disturbing the patient, and without requiring intermediate action by a paging supervisor to activate pagers in response to the alarm.

A further disadvantage of prior art pagers is their limited capability for providing information to the user and for enabling that user to respond quickly and effectively. Typically, pager communications are limited to providing an audio tone coupled with a lighted display. The alarm produced by the pager may also contain an image of a phone number that the wearer is supposed to call in response to the alarm. One drawback to such pagers is that the person wearing the pager is not informed of the actual nature of the problem until he/she telephones the sender. In those instances where a phone is not readily available to the paged party, critical response time is lost possibly endangering the patient's life. Thus, a need exists for a paging device that communicates detailed information about the patient and allows for a rapid response by the recipient.

A further disadvantage of conventional pagers is that the information must be relayed to the recipient through other personnel. There is thereby some risk that inaccurate information may be conveyed to the doctor particularly when the medical staff conveying the information is under pressure and stress. Miscommunication is exacerbated in emergencies, such as "code blue" alerts. A need thereby also exists for a paging system that communicates information directly from critical medical equipment to the recipient avoiding the possible delay and miscommunication by an intermediary.

Conventional pagers also are limited to only receiving messages. However, the message recipient frequently needs to urgently communicate to others. A pager having a two-way communications capability is thereby essential in many emergency situations.

Another drawback of conventional communications devices is the relative inconvenience of two-way walkie-talkie RF devices used principally by emergency medical technicians to communicate with one another, and with the hospital emergency room. Typical walkie-talkie arrangements consist of a speaker/microphone attached to a transceiver and power supply which are all arranged in the same cabinet. The speaker and microphone design, however, has several drawbacks. First, critical messages are often relayed to emergency medical personnel loudly and intrusively causing possible debilitating distress to the patient. Second, the structural arrangement of walkie-talkies is inconvenient since the user must physically place the walkie-talkie close to his mouth when speaking. Thus, at least one hand is occupied operating the walkie-talkie. In an emergency where the emergency medical technician is under severe time constraints to perform CPR or to move an injured person as well as communicate with the emergency room, the loss of one hand can be a severe detriment.

Finally, many paging/emergency communications systems fail to coordinate automatically and flexibly with the variable staffing conditions. Thus, if necessary staff are either not "on call" or are preoccupied with other more urgent medical situations, there is a need to provide a fail-safe management device for routing calls to available staff so that quick responses to medical emergencies can be maximized and so that a response is provided to a person in need at all times.

The present invention overcomes the problems of the prior art by a communications/alarm system for providing secure, efficient and reliable communications concerning the medical conditions of patients and the status and operational conditions of any medical equipment that may be used in a pre-hospital, post-hospital or in-hospital setting. The present system is designed so that communications do not disturb or traumatize the patient. Only necessary hospital personnel, such as doctors, nurses or technicians responsible for the patient and the life support equipment, are alerted. Information is conveyed silently by using vibration annunciation, specially designed lighted displays, or communications devices that have minimum audio warning features.

The displays delineate the specific patient having problems, specific defective equipment, the patient location and/or designation, the equipment name, or other relevant information read directly off of the equipment. In addition, a communications management system is provided which flexibly links hospital staffing circumstances with the medical needs of various patients.

SUMMARY OF THE INVENTION

This invention relates generally to a patient monitoring, communications, management and patient life support equipment alarm system that is non-audible and unobservable to the patient and that is used to notify doctors, nurses and/or technicians that a patient has a medical problem and/or that medical equipment is malfunctioning. The system can be employed in a pre-hospital, in-hospital and/or post-hospital setting.

The non-audible communications system in accordance with the invention is comprised of an electronically actuated signal generator attached to a device sensor(s) connected to any appropriate medical equipment and/or patient monitoring or operating room equipment, at least one master alarm control and display unit adapted to communicate with the signal generators and/or with other master alarm control units and a central host controller. Each master alarm control device can be removed from the patient area and located preferably at a nurses' station. In some applications, the master alarm control can be located in the operating room, the emergency room or at any other desired location. Multiple master alarm control devices can be tied together in a network. An appropriate group of pagers that have non-audible annunciators are also part of the system.

Each master control and display unit includes suitable logic and memory to store information concerning the availability of medical staff so that the master control can manage incoming emergency calls by matching those calls with available staff. Typical support equipment to which the communications and alarm system is attached include in-hospital equipment such as IV feeders, ventilators, cardiogram monitors, $CO_2$ machines, fetal monitors, pulse monitors, blood pressure monitors, or other life support, patient monitoring devices or operating room equipment such as heart/lung machines; pre-hospital equipment used in emergency and non-emergency settings, such as pulse monitors or defibrillators; and post-hospital equipment used, for example, in patient's homes, in nursing homes, in hospices, in doctor's offices or in teaching establishments.

Certain life support equipment and patient monitoring equipment demand an immediate response and are of particular concern. A defective ventilator can immediately stop a patient from breathing. An IV feeder, if interrupted, can be life threatening. Cardiac, pulse and blood pressure monitoring systems demand immediate responses if the patient is in trouble. The need for immediacy is also critical in an operating room environment where the loss of several seconds may cost a patient's life. The system forming the present invention may also be used to replace or augment the overhead audio paging system to provide non-audio messages to summon a particular doctor to a specific destination. Intelligence is programmed into the master alarm control part of the system by virtue of the logic associated with the master alarm control unit and by virtue of the use of a suitable operator who communicates with the medical personnel, the hospital administrators, and most importantly with the patient to alert appropriate staff based upon changing conditions and preferences.

The alarm component of the invention comprises an alarm signal generator that receives electrical output signals from a conventional equipment alarm sensor(s) which is non-audible indicating that a patient is in trouble or equipment is defective or shut down. The alarm signal generator has its own power source and is in communication with the master control and display unit or units.

The alarm signal generator transmits a coded pulse signal in response to a sensor(s) signal indicating a problem and provides various identification information such as particular patient and/or equipment type and location for display on the master control and display unit. Immediate transmission from the master unit or units then occurs to an appropriate group of pagers carried by doctors, nurses and technicians. In addition to the alarm generator, an information communications control module can be arranged on the medical device so that the same information available to the medical equipment operator can also be communicated to the master control and display unit or units and to the pagers through a suitable cable connection or through an RF-based receiver/transmitter.

The alarm and communications system is designed so that the alarm signal generator, the master alarm control and display unit or units, and the pagers and walkie-talkies cannot provide an audio or visual alarm to the particular patient in trouble. An audio alarm may be utilized in addition to the visual display at the master control and display unit provided that the audio alarm sound cannot be heard by the patient. The alarm signal generator includes a manual call-for-help switch that can be activated by a person at the bedside to summon additional help without a sensor(s) signal to activate the alarm. Alternatively, the call-for-help can originate from the pager worn by personnel in need of assistance. Thus, the nurse can directly page the physician from the patient's bedside without delay and without alarming the patient. In the event that incorrect pager numbers are entered by, for example, the bedside, or by the operator of the master alarm control unit, the system contains a pager number list to provide immediate feedback to the nurse/operator of an incorrect entry. Users of the system also can access the table list by the name of party associated with the desired pager, in order to look up the correct pager number.

The system may include an additional alarm visual display panel in the room of the patient hidden from the patient's view. In such case, the alarm visual display would be located so that a lighted panel with lights indicative of a patient problem or equipment malfunction will not be observable by the monitored patient, but would be visible to hospital and medical personnel located in the room to indicate a patient monitor warning or equipment failure. Also, an indicator is provided on the equipment out of the view of the patient to identify the malfunctioning equipment.

The pager is a component of the invention. In accordance with the invention, an appropriate group of specially designed pagers is utilized to alert, non-audibly, doctors, nurses and technicians in conjunction with the master control and display unit which transmits a coded alarm signal to the appropriate pager in the appropriate group of pagers. The appropriate group of pagers has a conventional vibrational annunciator. Also, the appropriate group of pagers contains, in addition to the conventional RF signal receiver and signal processing circuitry, a lighted liquid crystal display (LCD) or light emitting diode display (LED) that gives instant information as to the location, patient name, equipment identification and/or other relevant information provided directly from the medical equipment, if desired. The coded alarm signal provides the information which is processed in microprocessor circuitry to actuate an array of lights and/ or liquid crystal or LED elements which make up the display face on the pager. The display could also include a "code blue" indication requiring an immediate response from all available personnel. A keyboard containing alphanumeric keys and soft-coded function keys is arranged on the pager to enable the user to communicate messages to the master alarm control, and to other pagers.

The pager can also be arranged so that it is worn on the user's wrist in much the same manner as a digital wristwatch.

Another important element of the invention is an alarm signal interrupt switch located both on the sensor(s), which is attached to the equipment at the site of the patient, to the alarm signal generator which is adjacent to the medical equipment and/or on the master alarm control device. The alarm signal generator, once activated by a patient problem or equipment defect, will not stop until one of the above-noted interrupt switches is unlocked and manually actuated, insuring that the patient will not be inadvertently ignored or forgotten. The interrupt switch can be either a timed switch that returns to a deactivated position when timed-out by a suitable timing mechanism or a momentary switch that deactivates when released. The status of the interrupt switch and the time period for the interrupt switch may be set by an operator of the master control unit who has appropriate clearances to unlock the interrupt switch. An interrupt condition and either the time-out period remaining for that interrupt or the time expired by that interrupt may be displayed by the master control unit.

A further feature of the present invention is a walkie-talkie communications system that is used in conjunction with the equipment monitoring and master control units. The walkie-talkie system is designed so that emergency technicians and medical staff can receive effective communications from ambulances regarding both the patient's condition via direct information from medical equipment monitors and audio messages from emergency personnel (e.g. medical technicians, ambulance drivers, police, fire rescue personnel, etc.) through a walkie-talkie device worn by an emergency personnel.

The rescue walkie-talkie equipment has a privacy function so that all communications would occur quietly without causing undue stress to the patient or others. The walkie-talkie arrangement includes a microphone and headset piece which are designed to muffle ambient noise levels and to ensure complete privacy of communications. The walkie-talkie design thereby maximizes the patient's privacy by reducing stress created by hearing the communicated information.

It is an object of the invention to provide an improved alarm and communications system for patient monitoring and life support equipment used by patients in pre-hospital, in-hospital and post-hospital settings such that the communications and/or alarm resulting from a patient in trouble or defective equipment will not be heard or seen by the patient to prevent patient trauma.

It is another object of this invention to provide an improved alarm system for critically ill patient monitor and life support equipment that alerts only authorized medical personnel according to current hospital staffing at the moment the alarm is generated without alerting or disturbing any of the patients including the person being monitored.

And yet still another object of this invention is to provide a silent patient monitor and life support equipment system that eliminates trauma to the patient while not reducing the efficiency of the staff to respond appropriately.

In accordance with these and other objects which will be apparent hereinafter, the instant invention will now be described with particular reference to the accompanying drawings.

BRIEF DESCRIPTION OF THE DRAWINGS

FIG. 1 shows a schematic diagram of one embodiment of the present invention;

FIG. 2 shows a typical pager display face which may be used with the present invention;

FIG. 6 is a perspective view of the walkie-talkie headset arrangement according to the present invention;

FIG. 7 is a front detailed view of the microphone mouthpiece of the headset shown in FIG. 6.

PREFERRED EMBODIMENT OF THE INVENTION

Figure 3:
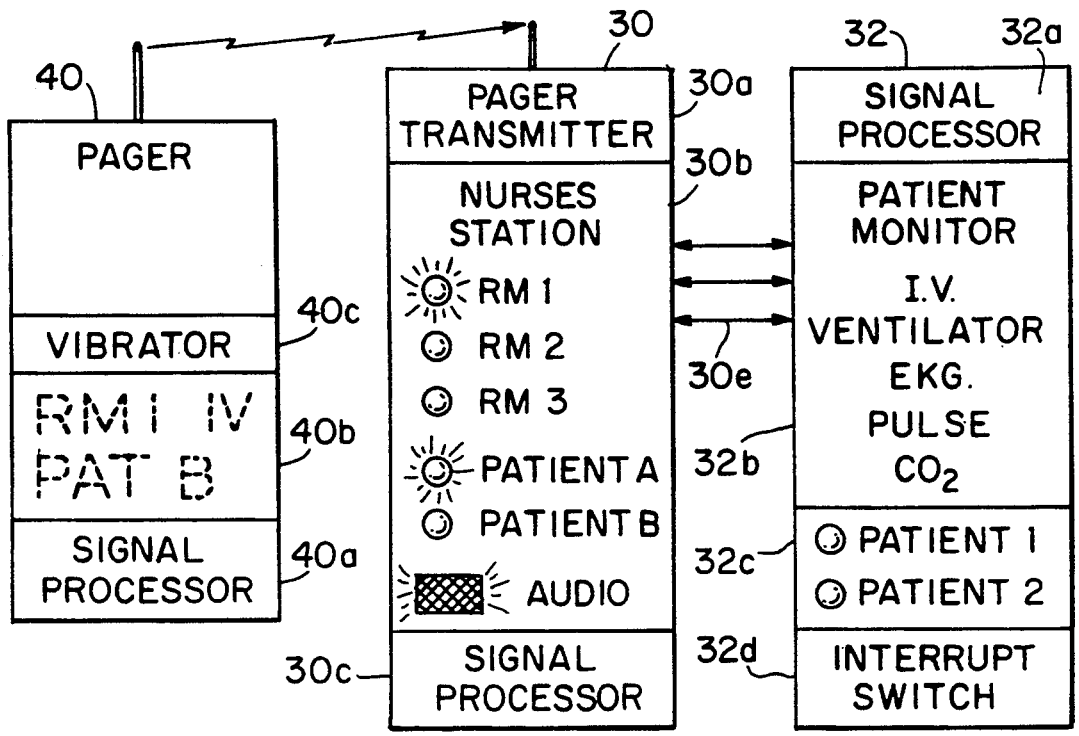
FIG. 3 is a schematic diagram of the silent alarm system utilized in the present invention.

Referring now to the drawings wherein like reference numbers refer to like parts, and specifically FIG. 1, the present invention is shown schematically comprising an alarm signal pulse generator 12 which receives a status output signal from medical equipment and a sensor 10 that provides a signal when the equipment sensor(s) indicates the patient is in trouble or in the event of a malfunction of the equipment. Although conventionally some of the equipment using sensor 10 would include an audio alarm, applicant's invention would eliminate any type of audio and/or visual signal that could be heard or seen by the patient attached to the equipment.

The sensor 10 is adapted to be used with pre-hospital equipment such as those devices employed on ambulances, or at the site of an accident, or in emergency rooms, or in doctor's offices, or in clinics. The sensor(s) can also be attached to equipment used in the hospital, such as patient monitoring and life support equipment found in the patient's room, such as in a hospital recovery ward, or life support equipment used in the operating room. Equipment used in post-hospital settings such as in nursing homes, or in hospices or at the patient's home, or in medical educational settings are also adapted to be used with the sensor(s). The communications system can also be used in hospital administration environments, such as in the emergency room admissions desk.

The specific types of equipment can include, but are not limited to, defibrillators, oximeters, EKG monitors, EEG monitors, intravenous feeding devices, ventilators, pulse monitors and any other equipment used in the above-noted environments.

The sensor 10 is designed to have an adaptable sampling rate based upon the type of equipment that it is sampling. For example, a ventilator may require a sensor with a very high sampling rate (e.g., every 1-2 seconds) while an IV monitor may only be sampled every fifteen minutes. Hence, the sensor 10 can be adjusted to vary the sampling time period accordingly. The sensor(s) is also adapted to be connected directly to the alarm indicator hardware that is found on the specified equipment so that alarm thresholds identified by a particular equipment manufacturer may be communicated automatically by the sensor 10.

The alarm signal pulse generator 12 takes the status output signal from the equipment monitor sensor 10 and converts that signal into a coded pulse that identifies the patient, the room, the ambulance or other relevant location information. The equipment type for which sensor 10 denotes a problem is also identified along with readings from the equipment.

The output of the alarm signal pulse generator 12 may be communicated through a conventional electric wire or optical cable to the master alarm control 14 typically located at a nurse's station. Alternatively, communications from generator 12 can be RF-based through conventional RF emergency bands (such as those designated for ambulances) or for emergency medical personnel. If the sensor 10 and generator 12 are used in a patient's home or at a doctor's office, then the generator 12 can be connected, for example, through a modem or other communications devices to a phone linked directly to the master control and to the display. Another example of suitable home use for the signal generator 12 is in combination with a Halter monitor for sensing EKG life-threatening arrhythmias, which can be sensed at the master control unit 14 and communicate to each of an appropriate group of pagers worn by those responsible for this patient. Thus, the present system encourages the release of patients since they can be monitored at home.

If, for example, a signal generator 12 is located on each ambulance affiliated with a single master alarm control and display 14, then a separate RF band for each ambulance can be assigned to avoid communications delays. Individually assigned RF bands can also be used to designate each patient's room in the hospital.

In addition to signalling the master alarm control, the pulse generator can be programmed to simultaneously communicate with the pagers in order to avoid delays. Thus, if a patient, who is having heart problems, is being rushed to the hospital, the EKG information can be communicated directly to the master control display while the pulse generator also alerts the cardiologist via his/her pager assigned to the emergency room about the incoming patient. If the patient is attended to after the pager is initially activated, the pager can be updated as the patient's condition changes.

A further function of the pulse generator 12 is it's ability to test the equipment for malfunctions. Tests can be initiated from the master alarm control 14 so that the controller operator can display the equipment status remotely. Thus, to test emergency equipment located in each car of a fleet of ambulances, each RF band can be separately selected by the operator of the master control 14. The respective pulse generator 12, associated with that identified band is addressed and then in turn responds to the initiation signal sent from the master control 14 by identifying the ambulance and associated equipment. The master control 14 then signals the pulse generator 12 to activate the emergency equipment and to test it's condition through sensor 10. The self-test function can also be initiated from the pager 16, 18 or 100 or from the technician's walkie-talkie. Once tested, equipment status can be communicated back to the master control 14.

The master control 14 also includes a visual display that provides relevant information such as patient location, patient condition and the type of equipment requiring a response. The master control 14 includes an antenna 14a to simultaneously transmit a signal to an appropriate group of pagers 16 and 18, and 100 (see FIG. 8) each of which have antennas 16a, 18a and 122, respectively. The appropriate group of pagers 16, 18 and 100 has a vibrational annunciator in lieu of or in addition to audio annunciator capabilities so that the wearer, once feeling a vibration, will position the pager for visually observing a display face having visual indicia. As shown on pager 16 and pager 18, a series of lights may be provided to show room and patient identification that require immediate response. Alternatively, lights can be arranged to indicate other information, such as ambulance number or patient's phone number. In addition, other lights can be provided to show what equipment type needs immediate response and/or other relevant information.

In addition to pagers, the master control 14 can interact with walkie-talkie communications devices (see FIGS. 6–7) which are adapted to receive and transmit voice communications from emergency medical staff in conjunction with or completely independent of the medical equipment alarm discussed above. Communications occur either through speaker/microphone 15 which forms part of the control unit 14 or through a headset 80 or any other conventional headset arrangement, which ensures the privacy of communications. The speaker/microphone 15 allows multiple individuals to speak through the microphone at the same time. Alternatively, the speaker/microphone 15 can be connected to the hospital intercom system. Further details concerning the headset 80 are set forth below in FIGS. 6–7.

The master control 14 is designed to be programmable by the operator in order to store information relevant to achieving a prioritized and efficient communication with minimum human intervention so that speed, privacy and efficiency are maximized.

Figure 5:
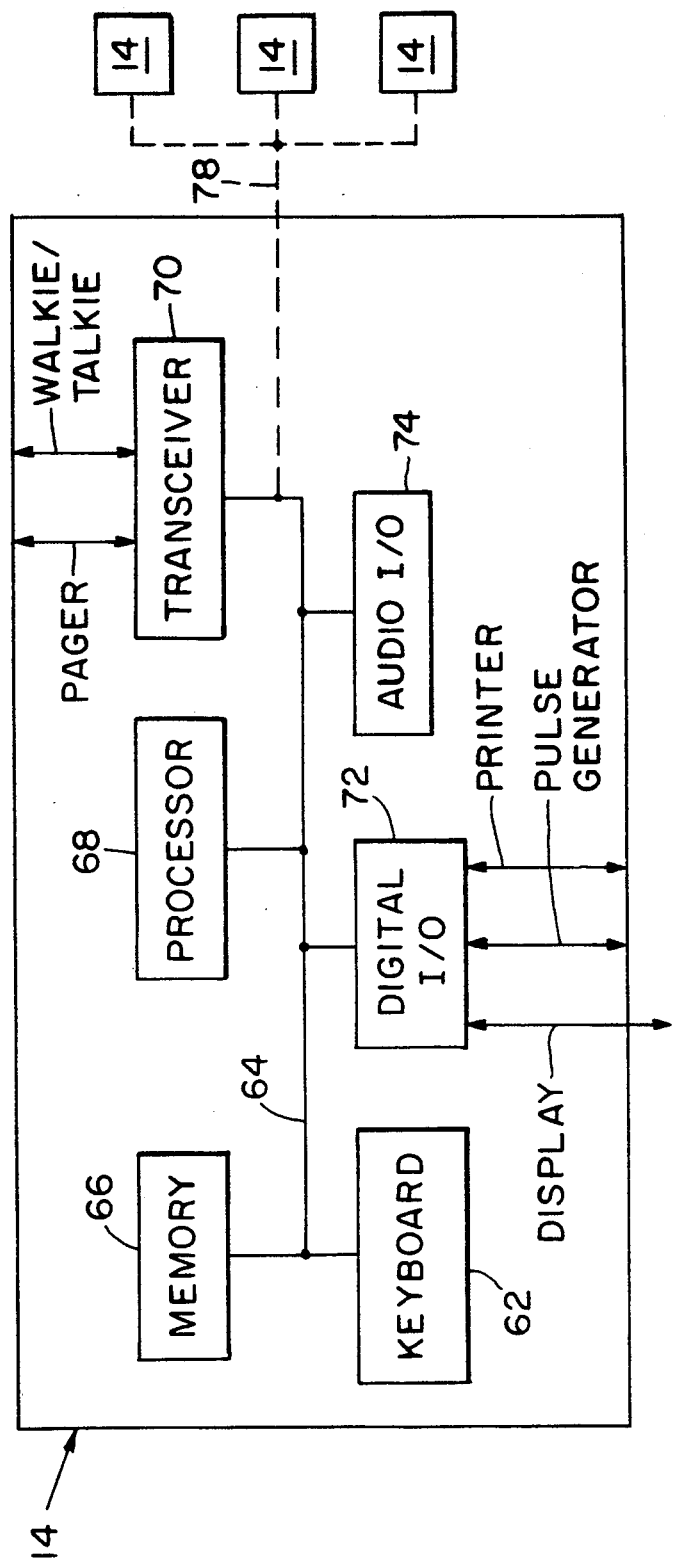
FIG. 5 is a schematic block diagram of the master control unit shown in FIG. 1.

More particularly, the arrangement of the master control 14 is shown in more detail in FIG. 5. As shown, the master control device is arranged to provide programmable control for scheduling and prioritizing communications in accordance with the staffing realities of the hospital. In order to input current information into the system, the user operates a keyboard 62. The information provided includes the names of hospital staff assigned to each patient, to each room, and to each type of medical condition as well as the availability of those individuals to respond to emergency calls. Thus, if the doctor assigned to the patient is attending to another emergency, the system flexibly assigns an alternate doctor who is available and/or who specializes in the condition indicated by the equipment. Other critical medical data or personnel can also be included in the master control 14. For example, the telephone and/or pager number of the original doctor can be inputted so that the original physician can be notified and consulted. Medical data integrated in the device can include all information found on the patient's chart including laboratory test results. It is contemplated that a computerized system that incorporates laboratory test results can form part of the present invention. As an example, the ALERTS system reported by M. M. Shabot et al. in "Decision Support Alerts for Clinical Laboratory and Blood Gas Data" in the International Journal of Clinical Monitoring and Computing 7, pp. 27–31, 1990, would form part of the data which can cause alarm conditions to be automatically communicated to the master control 14 and be communicated to pagers based upon the ALERTS thresholds. Data relating to the ALERTS database could be provided the master control unit 14 through the hospital database. The pager number is then automatically called by the device so that communications occur automatically to appropriate hospital staff with minimal intervention by the main control operator.

In addition to paging personnel and medical data, the master alarm control device includes prioritizing algorithms which act as messaging traffic controllers for the system. Thus, in the event that a code blue condition is communicated, the system interrupts other lower priority messages to immediately communicate the "code blue" messages.

The keyboard 62 is connected via a bus 64 in the master control 14 to a memory 66. Any suitable RAM and ROM and/or high speed semiconductor memory device (i.e. such as a scratch-pad or cache memory) can be employed to quickly retrieve the stored availability information, as needed. The stored data is then processed by a CPU 68 in order to perform the appropriate logical operations on the stored data (such as choosing the RF band for the transceiver 70, for interpreting equipment readings, for selecting available staff based on a priority determination). The input/output operations of the master control 14 are handled by the digital I/0 unit 72 which receives digital signals from the pulse generator 12 via the cable link 13. Additionally, information presented on display for the master control 14 or printed out to an attached printer can also be provided. An audio I/0 unit 74 is used to control information sent to and received from other audio equipment (such as a walkie-talkie headset, or by telephone).

The RF bands available to the master control device may vary depending upon the particular environment in which the system is placed. If, for example, the master control unit is used to communicate with ambulances, then the RF band selected for transceiver 70 is an emergency RF band. The selection of RF bands will be controlled through the keyboard 62 which causes the transceiver 70 to adjust to a frequency identified by the operator. Thus, the master control unit can operate at multiple frequencies, making it flexible. For example, if several master control units are employed in the same facility, such as placing one in the operating room and one in the emergency room and one in the cardiac care unit, then different RF bands can be assigned to different master alarm units to avoid interference.

In operation, for example, should a patient monitor, such as a pulse or blood pressure monitor, fall below a threshold limit, sensor 10 will provide a status signal indicating that there is a problem to the alarm signal pulse generator 12. A coded pulse signal is then prepared and sent to the master alarm control 14 either through the hard-wired cable 13 or phone/modem line, or through RF antenna 12a. The master control 14 simultaneously displays the information contained in the coded pulse with regard to room, patient and equipment on a visual display at the nurse's station while the system also transmits simultaneously the coded message to the appropriate group of pagers.

As will be described in further detail below, the adaptability of the system to communicate over different RF bands is also reflected in the pagers which can be switched from one frequency to another. Accordingly, if a physician works at home, and communicates at home to a modem at one frequency, he can change his pager RF band to the master control frequency for his ward, and then adjust it again to match the band of the master alarm unit used in the operating room.

The system can also accommodate a network of master alarm control units connected to one another through a conventional network, such as ETHERNET ®. Thus, scheduling personnel and medical data information can be shared between units 14 making the changing needs of the patient and changing conditions of the hospital more closely attuned to one another. Thus, if a patient is moved from the operating room (OR) to the cardiac care unit (CCU) and then from the CCU to the general medical recovery unit, all information pertaining to that patient can be communicated across the network 78 to the master alarm control unit 14 responsible for that respective area. Thus, for example, the recovery room personnel can observe the condition of a patient in OR prior to receiving that patient in recovery and prepare for that patient's arrival.

Another example of master alarm control unit 14 placement would be to assign a master alarm unit to monitor all signals for a particular type of equipment. Hence, all ventilator outputs could be handled by one unit 14, while all EKG units could be handled by a separate unit 14. The number of units 14 can be adjusted to meet the needs of the ward, of the floor and of the institution as a whole. The unit 14 can also be placed in doctor's lounges, when appropriate.

Operation of the master alarm control unit 14 can rely on a capable medical operator who can both insure security, maintain priorities and update all information. Operators having different levels of training can be assigned to different master alarm control units 14 or multiple operators, each having a different level of responsibility, security clearance and experience can be assigned to a single master control unit. In the event that multiple emergency conditions are activated for the same physician, the presence of the operator can ensure that the back-up person with the right expertise can effectively respond to the alarm.

As an example, if the master alarm control unit is used in an operating room (OR) setting, then an individual who should, in most instance, be a physician, may be assigned to simply monitor the status of all of the OR equipment on the display, while each of the physicians in charge of respective pieces of equipment wear pagers that are energized when an alarm occurs. The operator at the master alarm control in the OR can interrupt false equipment alarms to avoid unnecessary alarms to the physicians. Since the display of unit 14 thereby integrates the outputs of all OR equipment, a single individual can oversee the entire physical condition of the patient through the unit 14 and also page essential personnel who are outside the OR in the event extra help is needed. The system is also designed to only restrict audible communications of equipment alarms, but can maintain the normal auditory signals indicating, for example, that all is well with the patient.

FIG. 2 shows one embodiment of a pager 20 of an appropriate group of pagers. The pager 20 which includes a plurality of lights 20a that indicate information silently by illuminating the particular room where the patient with life support equipment needing response is located. Likewise, additional lights 20b represent the particular patient within the room requiring response. The light indication is augmented through a vibration annunciator located on the pager 20.

Referring now to FIG. 3, an alternate embodiment of the invention is shown. The alternate embodiment includes an alarm signal pulse generator 32 that receives, as an input, the output signal from patient monitors, which include, but are not limited to, IV feeders, ventilators, EEG devices, EKG devices, $CO_2$ measuring devices. The pulse generator includes a signal processing unit 32a that can receive an alarm signal from a sensor(s) located on any type of equipment indicating that a malfunction or patient problem exists. The signal processor converts the signal into a coded pulse which is transmitted by cables 30e or by suitable RF communications to the master control 30, typically located at a nurses' station. The master control 30 includes a display face 30b that comprises lights with room numbers, patient identification and may include an audio microphone/speaker if the master control station is located far enough away from the patients so that the audio signal could not be heard or found disturbing. The display 30b can include the more sophisticated information as shown and described with respect to master alarm control unit 14 in FIGS. 1 and 5. The master control 30 also includes a pager transmitter which sends an RF signal which is coded to the appropriate group of pagers 40.

Each of the appropriate group of pagers, in turn, has a visual display 40b which may be constructed of a liquid crystal display or light emitting diode display positioned on one face of the pager. The annunciator in the pager comprises a kinesthetic vibration caused by a vibrator 40c located in the pager. The pager also includes appropriate signal processing circuitry to drive the display face 40b and the vibrator unit 40c. The pager can also provide information to silently summon a specific doctor to a particular location.

Various parts of the system, the master alarm control unit 14, the sensor 10 and the alarm signal pulse generator 32, as shown in FIG. 3, also include an interrupt capability for deactivating the alarm signals produced by the system upon activation of the alarm switch. The purpose of the interrupt switch is to block the alarm signals for either a particular piece of equipment, for an entire room full of equipment or for even larger areas in the event the person having proper security clearances believes that an interrupt is necessary. The importance of the interrupt switch is it's ability to disarm the alarm for a malfunctioning device, to shut off the alarms relating to all of the equipment attached to a patient (suppose the patient is moved which trips all of the monitors attached to him/her) or to disconnect an entire floor of equipment (suppose a technician sets the thresholds for all EKG devices in the hospital too low causing continuous alarms).

Referring to FIG. 3 a main alarm interrupt switch 32d is shown for selectively interrupting signals generated from equipment. The interrupt switch 32d is guarded by a lock (i.e., a number combination, or a user security number if set through the master control) so that the switch can only be activated when unlocked. The lock is necessary to prevent unauthorized individuals from turning off equipment. In addition, the alarm generator signals can only be terminated by physically moving the main switch 32d momentarily located on the alarm signal generator connected near the patient bedside to the patient monitor or life support equipment so that the patient must be attended to in order for the alarm to be turned off.

An interrupt switch can also be placed on the sensor 10 (not shown) so that it is located physically close or adjacent to the interrupt switch used on the medical equipment itself. As a result, the nurse or physician can easily turn off the equipment and turn on the interrupt switch without undue inconvenience. In addition, the interrupt switch can include a lock to safeguard against unauthorized staff from disabling equipment. Activating the interrupt switch terminates the coded pulse signal initiated by the sensor(s) signal for that specific piece of equipment. The interrupt switch, once released, or turned off, returns the alarm signal pulse generator to its normal activated state ready to respond to a new incoming sensor(s) signal.

The interrupt switch may be a toggle switch that is spring loaded to the "on" position and may include a timer circuit. The interrupt status can also be displayed on the master alarm control 14.

An interrupt switch with a suitable lock may also be located on the master alarm control 14 to selectively interrupt individual equipment, all equipment in a patient's room, or all rooms in a given ward. The alarm control can be programmed so that each higher level of interrupt requires additional locks or higher level security access to the unit 14. An individual nurse, for example, may be allowed only to interrupt one piece of equipment while only the head nurse or resident on duty can disable an entire ward. The security access element of unit 14 can consist of any conventional password software lock, or a combination of mechanical key and software lock elements.

In addition, located in the patient's room out of the vision of the patient, is a display 32c which could show an attendant in the room which patient and/or equipment demands attention or requires a response. For example, a red light indicating an alarm can be located on the equipment out of the patient's view.

Figure 4:
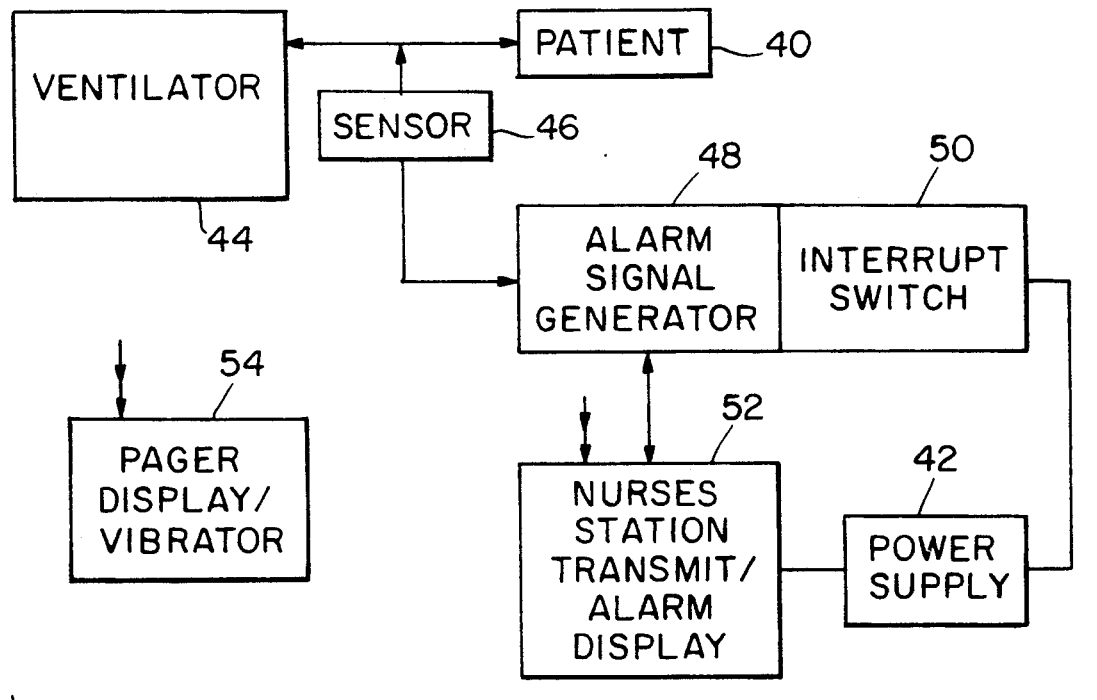
FIG. 4 is a schematic diagram using a ventilator life support system as an example of the alarm system in accordance with the invention.

Referring now to FIG. 4, a typical employment of the present invention is shown. A critically ill bedridden patient 40 is shown connected to a ventilator 44 and a sensor 46 which is a device known to provide a signal if the ventilator malfunctions or if there is a breathing problem with the patient. Although a ventilator is shown in this example, numerous other patient devices can be used individually or can be integrated together with the present invention.

As an example of a ventilator alarm that could be used with applicant's invention, applicant hereby incorporates the disclosure found in U.S. Pat. No. 4,550,726, issued Nov. 5, 1985, to McEwen which describes a ventilator monitor that produces an alarm signal if patient breathing is interrupted. The alarm signal is made to be inaudible for use with the present invention. The output alarm signal from the McEwen device would, as an example, be connected and represent sensor 46 in FIG. 4. The alarm signal generator 48 would then receive a malfunction signal from sensor 46 and transmit a generated coded signal to a nurses' station master control unit 52 located away from the patient. Any monitor, alarm system and sensor(s) utilized with the present invention will have any existing audible alarm disengaged. A conventional power supply supplies power to the alarm signal generator and to the remote master alarm control 52 located at the nurses' station.

The alarm signal generator 48 is capable of generating one or more individual coded pulses, each of which can be programmed on-site to individually identify, for example, the type of equipment, the patient location, such as a room or ambulance number, and the particular patient within a room. A programmable microprocessor alarm signal generator 48 can be set to generate a variety of coded pulses depending on a plurality of different inputs into the alarm signal generator. The coded pulses can originate from various different monitors and equipment sensors that relate to the types of equipment previously discussed herein which may be connected to a single patient or to multiple patients in a single room.

The master alarm control 52 simultaneously provides a display visually at the nurses' station that tells of the immediate problem and displays the patient room and equipment requiring response to the alarm signal, and transmits an RF signal to a plurality of pagers 54 having the visual displays described above and vibrational annunciators. The transmitted signals from the master control unit 52 could be coded in such a way that only particular pagers held by certain personnel would be activated or appropriate personnel on a particular floor or within a particular area as described above with reference to FIG. 5. For example, technicians that deal strictly with ventilators may have a certain code that would not disturb other personnel within a given area. Thus, only the appropriate personnel would be paged through their vibrational annunciators on their pagers. Non-essential or other personnel would not be disturbed. A high-level emergency or "code blue" signal could also be sent for a specific patient monitor or equipment problem.

In addition, the master control unit can be used to monitor the patient call or help system so that the member unit operator can energize an appropriate group of pagers when the patient call involves an emergency.

In another component to protect the patient, the alarm signal generator 48 includes an alarm signal interrupt switch, as previously described, for each piece of equipment in use, which must be manually activated at the patient's bedside to ensure that the patient or the life support equipment of the patient is attended to. Therefore, the coded alarm signal from generator 48 will continue at the nurses, station master control and display unit 42 and to the pagers 54 until the interrupt switch is momentarily activated at the patient location while the problem is being corrected.

To show the technology of a pager that includes vibrational output as an annunciator, applicant hereby incorporates the disclosure of U.S. Pat. No. 4,786,889 assigned to the NEC Corporation, issued Nov. 22, 1988. Although the invention described in FIG. 4 relates to a ventilator, all other types of life support equipment and patient monitors can be used with the present invention.

Other pagers with or without vibrational annunciators can be used with the present invention with the addition of the appropriate display. Additionally, those previously described pagers can incorporate transmitter/receiver devices so that direct two-way communications between the pagers and the control device 14 are available.

Referring now to FIG. 6, a perspective diagram of a headset microphone arrangement 80 is illustrated. The purpose of this arrangement is to ensure that the privacy of verbal communications is maintained in order to reduce or avoid the panic physiology to the patient and/or others. An additional advantage to the headset arrangement is that walkie-talkie users may conveniently communicate with emergency room staff without having to physically hold the walkie-talkie. In the embodiment shown, the headset is adapted to plug into a walkie-talkie microphone-speaker jack. Alternatively, the walkie-talkie can be incorporated into the headphone as a single integrated unit. Thus, both hands of the emergency medical technician are available to treat the patient. Finally, the baffling on the microphone and earmuffs filter out background noise.

The headset arrangement 80 comprises a tubular headpiece 84 connecting a pair of headphones 82. Each of the headphones includes a speaker 83 surrounded by a circular cushion 85. Alternatively, the headset speaker can be insertable directly into the ear, without baffling and/or the microphone can also be arranged without the baffling material. The cushion can consist of any conventionally used headphone baffling material such as foam rubber, fabric, or plastic. The cushion surrounds a speaker (not shown) so that outputs of the speaker are only heard by the telephone wearer and outside noises are filtered out. The left earphone 87 is designed to swing between a closed position over the user's left ear (shown by solid lines) or to an open position (shown by dotted lines) allowing the headphone wearer to hear out of one ear. The swingable arrangement is accomplished by any conventionally known hinge connection in combination with an appropriate position locking means.

The tubular headpiece 84 extends below the left earphone 87 and connects to a mouthpiece 90. The shape of the mouthpiece is substantially oval to generally conform to the shape of the user's open mouth. The mouthpiece includes an internal microphone 96 (FIG. 7) surrounded by a cushion 92. As in the headphones 82, the cushion 92 provides privacy of communications by completely enclosing the microphone to the user's mouth. In addition, background noise is effectively eliminated so that communications are clearly received.

The mouthpiece 90 is connected to the headpiece 84 through a suitable, arrangement 88 in order that the mouthpiece can be pivoted towards and away from the user's mouth and adjusted so that it can be placed against the user's skin, thus enclosing his or her lips to ensure complete privacy of communications. As a result, the emergency patient, or other onlookers, cannot overhear remarks that may cause them undue stress. An example of the pivotable connection includes a spring loaded rotatable connection having detents for locking the microphone in a first position adjacent the user's mouth and a second position away from the user's mouth (e.g., below his/her chin).

Figure 8:
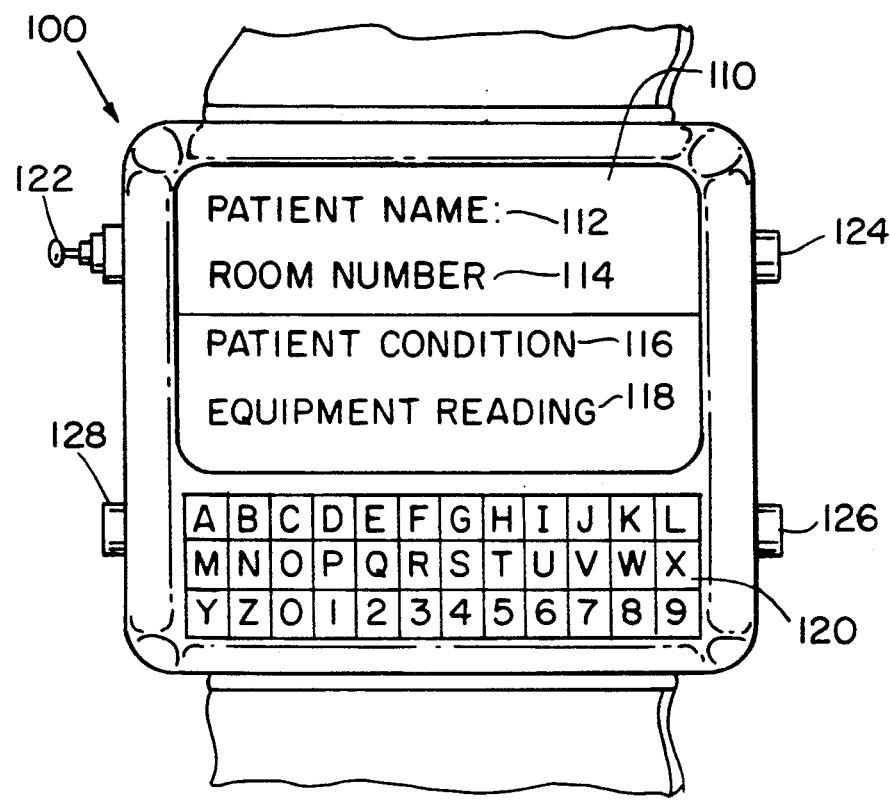
FIG. 8 is a front view of an alternate pager embodiment according to the present invention.

Referring now to FIG. 8, an alternate embodiment of the pager is illustrated. As shown, the pager comprises a wristwatch device 100 which may be conveniently worn by a user. The wristwatch pager consist of an LCD-type screen 110 which is subdivided to provide particular information about the patient's name 112, location 114, condition 116 and automatic equipment information 118. Any information can be displayed by the pager including detailed readouts from the medical equipment.

As a result of reviewing the screen, the wearer is automatically able to ascertain the location and condition of the patient and thus quickly access the urgency of the patient's condition and what actions need to be taken. The pager 100 includes a keyboard 120 which can be used by the pager wearer to send responsive messages back to the hospital through a transceiver linked to antenna 122. The pager can be linked to any cellular network through antenna 122, so that responsive phone calls to the hospital can be made from any location within the cellular network.

The pager further includes switches 124 and 126. Switch 124 acts to switch on the display receive mode so that the last displayed message is displayed. All messages that are received in a memory can be displayed in sequential fashion and can be sequenced through by multiple depressions. The message send button 126 controls the send mode. Upon a first depression, it clears the screen and provides an edit mode which allows the wearer to type in a response and when pressed again, switches into a send mode for sending the message through the antenna 122. The pager thereby automatically allows for silent information based communication with little need for the physician to find a telephone. As a result, critical time is saved while a maximum amount of information is automatically sent and retrieved.

In addition to sending return communications to the hospital, the pager 100 can also transmit information to other pagers. Thus, if a doctor determines that he would need assistance on an emergency basis, he may call other pagers remotely from his own pager and provide an informational message describing the content of the condition and the locale of the problem. Special codes can also be set up for automatic messaging. For example, if a "code blue" condition occurs, a single button can be pressed by the master control 14 to automatically actuate either an audible, kinesthetic or visual message to the pager.

If a silent mode of operation is desired, the user can activate an annunciator control button 128 which enables the user to select between an audible announcement or a vibration annunciation of the message. In a hospital setting, the doctor may want to deactivate any loud audible tones generated by the pager so that only a vibration is sensed. On the other hand, if the audio button 128 is activated, a loud beeping sound would occur at a particular frequency for standard messages and a different frequency for emergency "code blue" type messages.

The invention thus provides a non-audible alarm indicative that a critically ill patient is in need of an immediate response. Only the appropriate doctors, nurses and technical personnel will be immediately summoned. The patient will not be startled or even have knowledge that an alarm has been issued. This will prevent trauma to the patient and will also aid other patients in the vicinity to prevent them from being disturbed by alarms for the same reasons. Other critical problems thus solved by this invention include interfacing personnel through wrist band pagers with equipment on sites, interfacing professionals outside of the hospital with equipment alarms for their patients when on call in addition to in-house staff, paging people in order to transmit medical information as well as contacting the individual staff who must respond to the communication.

The instant invention has been shown and described herein in what is considered to be the most practical and preferred embodiment. It is recognized, however, that departures may be made therefrom within the scope of the invention and that modifications will occur to a person skilled in the art.

What is claimed is:

1. A communications system for medical use, comprising:
    medical equipment associated with a patient;
    alarm signal generator means in communication with aid equipment for generating an alarm signal, said alarm signal identifying said equipment and readings from said equipment;
    control means for receiving said alarm signal and for displaying indicia relevant to patient location, patient identification and equipment readings associated with such patient;
    said control means having a means for transmitting a pager message to at least one paging means in the form of an identifying signal, said identifying signal providing each of said at least one paging means with information relevant to said equipment and such patient; and
    each of said at least one paging means having a visual indicia display, means for receiving said pager message, and means for transmitting a response to said pager message to said control means.

2. A communication system according to claim 1, wherein each of said at least one paging means further comprises a vibrational annunciator means, each of said at least one paging means displaying visually relevant information concerning said patient and said equipment while also providing a vibration annunciation.

3. A communications system according to claim 2, wherein said visual indicia display further comprises an illuminated display screen for displaying indicia indicative of room, patient and equipment relating to the particular alarm signal requiring immediate response.

4. A communications system according to claim 1, wherein each of said at least one paging means is worn by a user.

5. A communications system according to claim 1, wherein said control means further comprises:
 key input means for providing messaging information to said control means;
 memory means for storing said messaging information;
 processing means for processing said messaging information and said alarm signal in order to prioritize messages and route said messages to appropriate personnel; and
 transceiver means for communicating said processed messaging information.

6. A communications system according to claim 5, wherein said messaging information comprises up-to-date staffing information relevant to all patients, said control means further comprises means to send said processed messaging information to appropriate and available staff.

7. A communications system according to claim 1, wherein said system is used with emergency medical services and ambulance equipment whereby said control means receives said alarm signal from emergency medical equipment used by medical services and ambulances.

8. A communications system according to claim 1, further comprising an audio communication means comprising a plurality of walkie-talkies; and
 a corresponding plurality of portable headsets each adapted to be connected to a respective walkie-talkie, whereby the privacy of communications between said plurality of walkie-talkies is ensured.

9. A communications system according to claim 8, wherein said plurality of walkie-talkies communicates with said control means, said system further comprising an additional headset adapted to be connected to said control means.

10. A communications system according to claim 1, wherein said system is used with equipment at any one or more of a clinic, a doctor's office, a hospital, a nursing home and a patient's home.

11. A communications system according to claim 1, wherein said alarm signal generator means provides said alarm signal directly to each of said at least one paging means and to said control means.

12. A communications system according to claim 1, further comprising:
 an alarm signal generator signal interrupt switch connected to said alarm signal generator means and located near said equipment, wherein said alarm signal, when generated by said alarm signal generator means, continues until said interrupt switch is activated.

13. A communications system according to claim 1, further comprising a messaging controller means for prioritizing said pager message such that a higher priority message will interrupt a lower priority message transmitted to each of said at least one paging means so that the higher priority message will be transmitted to each of said at least one paging means.

14. A communications system for medical use, comprising:
 a sensor attached to medical equipment associated with a patient for monitoring the status of said medical equipment;
 an alarm signal generator in communication with the sensor for communicating an alarm signal to a remote section;
 an alarm signal generator signal interrupt switch connected to said alarm signal generator and located near said equipment;
 wherein said alarm signal when communicated by said alarm signal generator continues until said interrupt switch is activated, the interrupt switch terminating said alarm signal for a period of time, the alarm signal reactivating at the end of the period of time if the sensor is in an alarm signal condition; and
 a call button for paging medical personnel from the patient's bedside.

15. An alarm system comprising:
 a sensor for determining a status of a plurality of conditions of a patient and an operational status of life support equipment;
 an alarm signal generator connected to said sensor and said alarm signal generator for transmitting said signals;
 an alarm controller connected to a signal receiver and remotely located from said alarm signal generator for generating an audio alarm and a visual alarm indicating patient location in response to said receiver receiving said signals, each alarm being generated at a location remote from the patient;
 processing means connected to said alarm controller for automatically selecting one of a plurality of remote displays for activation;
 a controller transmitter connected to said processing means for transmitting a radio frequency signal to said selected remote display for notification of selected personnel associated with said remote displays that said alarms have been generated; and
 an alarm signal generator signal interrupt switch connected to said alarm signal generator and located near the bedside of the patient wherein said audio and visual alarms when generated by said alarm controller continue regardless of the receipt of further signals until said interrupt switch is activated.

16. The alarm system as set forth in claim 15, wherein said alarm signal generator includes a timer circuit connected to said switch to automatically reactivate said alarm signal after a predetermined time.

17. The alarm system as set forth in claim 15, wherein said signals generated by said alarm signal generator include a coded electrical pulse indicative of relevant patient and equipment information.

18. The alarm system set forth in claim 15, wherein said alarm signal generator includes a manually-activated switch for generating an alarm signal.

19. The alarm system set forth in claim 15, further comprising a visual display unit located in the vicinity of said patient for indicating the status of said patient conditions and said equipment status.

20. A method for communicating medical information comprising:

receiving an electrical signal from medical equipment associated with a patient;

generating an alarm signal indentifying said equipment and readings from said equipment;

transmitting said alarm signal to a control means, said control means displaying indicia relevant to patient location, patient identification and equipment readings associated with such patient;

transmitting an identifying signal from said control means to at least one paging means with relevant information related to said equipment and such patient for visual display on an indicia display of each of said at least one paging means; and transmitting a response from any of said at least one paging means to said control means.

21. An alarm system comprising:

a sensor for determining a patient's condition;

an alarm signal generator connected to said sensor for generating signals indicative of said patient's condition and location;

an alarm controller connected to a signal receiver and remotely located from said alarm signal generator for generating an alarm indicating patient location in response to said receiver receiving said signals, said alarm being generated at a location remote from the patient;

processing means connected to said alarm controller for automatically selecting at least one or more remote displays for activation;

a controller transmitter for transmitting a radio frequency signal to said selected remote displays for notifying selected personnel associated with said remote displays of said alarm; and an alarm signal generator signal interrupt switch connected to said alarm signal generator and located near the bedside of the patient wherein said alarm, when generated by said alarm controller, continues regardless of the receipt of further signals until said interrupt switch is activated.

* * * * *